United States Patent [19]
Van Hoeven et al.

[11] 3,966,945
[45] June 29, 1976

[54] 2-ALKOXY(AND 2-ALKOXYALKYL)-2-HETEROCYCLIC-THIOACETAMIDES FOR INHIBITING GASTRIC ACID SECRETION

[75] Inventors: Helene E. Bowman Van Hoeven, Wallingford; L. Martin Brenner, Upper Darby; Bernard Loev, Broomall, all of Pa.

[73] Assignee: SmithKline Corporation, Philadelphia, Pa.

[22] Filed: June 12, 1975

[21] Appl. No.: 586,314

Related U.S. Application Data

[60] Division of Ser. No. 386,898, Aug. 9, 1973, Pat. No. 3,907,814, which is a continuation-in-part of Ser. No. 284,375, Aug. 28, 1972, abandoned, which is a continuation-in-part of Ser. No. 248,512, April 28, 1972, abandoned.

[52] U.S. Cl. ............................. 424/263; 424/250; 424/251; 424/258; 424/270; 424/274
[51] Int. Cl.$^2$ ........................................ A61K 31/44
[58] Field of Search ..................................... 424/263

[56] References Cited
UNITED STATES PATENTS
3,825,547  7/1974  Loev ............................. 424/263 X Primary Examiner—Frederick E. Waddell
Attorney, Agent, or Firm—Joan S. Keps; Richard D. Foggio; William H. Edgerton

[57] ABSTRACT

The compounds are 2-alkoxy(and 2-alkoxyalkyl)-2-heterocyclic-thioacetamides which are inhibitors of gastric acid secretion.

12 Claims, No Drawings

2-ALKOXY(AND 2-ALKOXYALKYL)-2-HETEROCYCLIC-THIOACETAMIDES FOR INHIBITING GASTRIC ACID SECRETION

This is a division of application Ser. No. 386,898, filed Aug. 9, 1973 now U.S. Pat. No. 3,907,814, which is a continuation-in-part of Ser. No. 284,375, filed Aug. 28, 1972, now abandoned, which is a continuation-in-part of Ser. No. 248,512, filed Apr. 28, 1972, now abandoned.

This invention relates to new 2-alkoxy(and 2-alkoxyalkyl)-2-heterocyclic-thioacetamides having pharmacological activity. In particular, these compounds inhibit gastric acid secretion.

The compounds of this invention are represented by the following formula:

FORMULA I

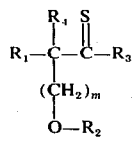

in which:

$m$ is 0, 1 or 2;

$R_1$ is 2-pyridyl, 2-pyrimidyl, 4-pyrimidyl, 2-pyrazinyl, 2-pyrrolyl, 2-quinolyl, 2-thiazolyl or 4-thiazolyl;

$R_2$ is lower alkyl, allyl or cyclopropanemethyl;

$R_3$ is

NH-phenyl or NH—$(CH_2)_n$-cycloalkyl, said cycloalkyl having 3–6 carbon atoms;

$R_4$ is hydrogen or lower alkyl;

$R_5$ and $R_6$ are hydrogen or lower alkyl and $n$ is 0 or 1.

This invention also includes pharmaceutically acceptable acid addition salts of the compounds of Formula I.

The pharmacologically active compounds of this invention have the basic structure of Formula I. However, it is apparent to one skilled in the art that well known nuclear substituents such as lower alkyl, lower alkoxy or halogen may be incorporated on the heterocyclic rings. These substituted compounds are used as are the parent compounds.

Preferred compounds of this invention are represented by Formula I in which $m$ is 0, $R_2$ is methyl, $R_3$ is NH-(lower alkyl), N(lower alkyl)$_2$ or NH—$(CH_2)_n$-cycloalkyl and $R_4$ is hydrogen or methyl.

Most preferably, in the compounds of Formula I, $R_1$ is 2-pyridyl. Also, preferably, $m$ is 0.

Particularly advantageous compounds of this invention are 2-methoxy-N-methyl-2-(2-pyridyl)thioacetamide and 2-methoxy-N,N-dimethyl-2-(2-pyridyl)thiopropanamide.

The compounds of this invention produce inhibition of gastric acid secretion. This activity is demonstrated by administration to pylorus ligated rats at doses of about 1.0 mg./kg. to about 50 mg./kg. orally or intramuscularly. Also, this activity is demonstrated by administration to chronic gastric fistula rats (Brodie et al., Amer. J. Physiol. 202:812–814, 1962) at doses of about 10 mg./kg. to about 50 mg./kg. orally. In these procedures, compounds which produce an increase in gastric pH or a decrease in the volume of gastric juice or both are considered active.

These compounds show antiulcer activity, for example in the restraint-stress method, in which an oral administration to rats these compounds inhibit the development of experimental ulcers.

The compounds of this invention are prepared by the following procedures:

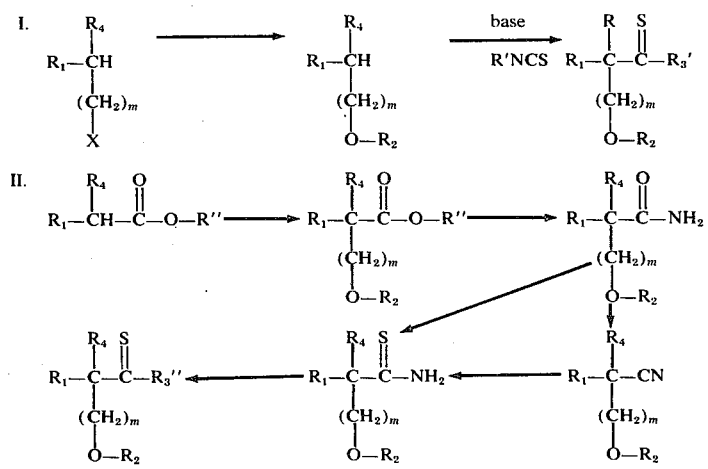

The terms $m$, $R_1$, $R_2$ and $R_4$ are as defined above, X is chloro or bromo, R' is lower alkyl, phenyl or $(CH_2)_n$-cycloalkyl, $R_3'$ is NH-(lower alkyl), NH-phenyl or NH—$(CH_2)_n$-cycloalkyl, R'' is lower alkyl, preferably methyl or ethyl and $R_3''$ is NH-(lower alkyl), N(lower alkyl)$_2$, NH-phenyl or NH—$(CH_2)_n$-cycloalkyl.

According to procedure I, a haloalkyl-heterocycle is reacted with an alkoxide, such as sodium alkoxide, and the resulting alkoxyalkyl-heterocycle is reacted with a strong base such as phenyl or butyl lithium and then with an appropriate isothiocyanate to give N-substituted 2-alkoxy(and 2-alkoxyalkyl)-2-heterocyclic-thioacetamides of this invention. The process of reacting an alkoxyalkyl-heterocycle with a strong base and then with an isothiocyanate to give N-substituted 2-alkoxy(and 2-alkoxyalkyl)-2-heterocyclicthioacetamides of this invention is also an object of this invention.

Alternatively, the alkoxyalkyl-heterocycles may be prepared by reacting a heterocyclic-alkanol with an appropriate halide, for example a lower alkyl, allyl or cyclopropanemethyl chloride or bromide, in the presence of a base such as sodium hydride.

According to procedure II, a lower alkyl 2-heterocyclic-acetate is converted to the 2-alkoxy compound by reacting with N-bromo or N-chlorosuccinimide and reacting the resulting 2-bromo or 2-chloro compound with a sodium alkoxide; the resulting lower alkyl 2-alkoxy(or 2-alkoxyalkyl)-2-heterocyclic-acetate is converted to the corresponding acetamide by reacting with ammonium hydroxide; the acetamide is dehydrated to give the corresponding nitrile and the nitrile is converted to a 2-alkoxy(or 2-alkoxyalkyl)-2-heterocyclic-thioacetamide of this invention by reacting with hydrogen sulfide in the presence of a base such as an amine or by reacting with ammonium polysulfide or, alternatively, the acetamide is reacted with phosphorus pentasulfide to give the corresponding thioacetamide of this invention. The N-substituted thioacetamides of this invention may be prepared by reacting the N-unsubstituted compounds with the appropriate amine.

The lower alkyl 2-alkoxy(or 2-alkoxyalkyl-2-heterocyclic-acetate intermediates in procedure II may also be prepared by reacting an alkoxyalkyl-heterocycle (which is an intermediate in procedure I) with a strong base such as phenyl lithium and a lower alkyl chloroformate.

Alternatively, the N-substituted thioacetamides of this invention may be prepared by the following procedures:

a. reacting a lower alkyl 2-alkoxy(or 2-alkoxyalkyl)-2-heterocyclic-acetate with the appropriate substituted amine and treating the resulting N-substituted 2-alkoxy(or 2-alkoxyalkyl)-2-heterocyclic-acetamide with phosphorus pentasulfide;

b. reacting an alkoxyalkyl-heterocycle with a strong base such as phenyl lithium and a N,N-di-lower alkyl-carbamoyl chloride and treating the resulting N,N-di-lower alkyl-2-alkoxy-(or 2-alkoxyalkyl)-2-heterocyclic-acetamide with phosphorus pentasulfide;

c. reacting an alkoxyalkyl-heterocycle with a strong base such as phenyl lithium and a N,N-di-lower alkyl-thiocarbamoyl chloride.

The pharmaceutically acceptable, acid addition salts of the compounds of Formula I are formed with organic and inorganic acids by methods known to the art. For example, the base is reacted with an organic or inorganic acid in aqueous miscible solvent, such as acetone or ethanol, with isolation of the salt by concentration and cooling or in aqueous immiscible solvent, such as ethyl ether or chloroform, with the desired salt separating directly. Exemplary of the salts which are included in this invention are maleate, fumarate, succinate, oxalate, benzoate, methanesulfonate, ethanedisulfonate, benzenesulfonate, acetate, propionate, tartrate, citrate, camphorsulfonate, hydrochloride, hydrobromide, sulfate, sulfamate, phosphate and nitrate salts.

The compounds of this invention are administered internally either parenterally, rectally or, preferably, orally in an amount to produce the desired biological activity.

Preferably, the compounds are administered in conventional dosage forms prepared by combining an appropriate dose of the compound with standard pharmaceutical carriers.

The pharmaceutical carrier may be for example a solid or a liquid. Exemplary of solid carriers are lactose, magnesium stearate, terra alba, sucrose, talc, stearic acid, gelatin, agar, pectin, acacia or cocoa butter. The amount of solid carrier will vary widely but preferably will be from about 25 mg. to about 1 gm. Exemplary of liquid carriers are syrup, peanut oil, olive oil, sesame oil, proylene glycol, polyethylene glycol (mol. wt. 200–400) and water. The carrier or diluent may include a time delay material well known to the art such as, for example, glyceryl monostearate or glyceryl distearate alone or with a wax.

A wide variety of pharmaceutical forms can be employed, for example the preparation may take the form of tablets, capsules, powders, suppositories, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The pharmaceutical compositions of this invention contain a compound of Formula I or a pharmaceutically acceptable acid addition salt thereof in an amount of from about 10 mg. to about 500 mg.

The methods of inhibiting gastric acid secretion in accordance with this invention comprise administering internally to an animal an effective amount of a compound of Formula I or a pharmaceutically acceptable acid addition salt thereof. The active ingredient will preferably be administered in dosage unit form as described hereabove. Preferably, the active ingredient will be administered in a total dosage of from about 10 mg. to about 2500 mg. Advantageously, equal doses will be administered one to four times per day.

When the administration is carried out as described above, gastric acid secretion is inhibited.

One skilled in the art will recognize that in determining the amounts of the active ingredient in the claimed compositions and used in the claimed methods the activity of the chemical ingredient as well as the size of the host animal must be considered.

It will be apparent to one skilled in the art that the compounds of this invention have an asymmetric carbon atom and thus may be present as optical isomers. The connotation of the formulas presented herein is to include all isomers, the separated isomers as well as mixtures thereof. Preferably, the optically active thioacetamides are prepared (a) by the use of optically active strong acids, such as camphorsulfonic acid or phenethylsulfamic acid, to separate the optical isomers of the thioacetamides or (b) by the use of optically active bases, such as α-methylbenzylamine or strychnine, to separate the optical isomers of 2-alkoxy(or 2-alkoxyalkyl)-2-heterocyclic acetic acids (prepared by hydrolysis of the esters prepared by the method described in procedure II) which are then esterified and converted to the thioacetamides according to procedure II.

The terms "lower alkyl" and "lower alkoxy" where used herein denote groups having 1–4 carbon atoms and "halogen" denotes chloro, bromo or fluoro.

The following examples are not limiting but are illustrative of the compounds of this invention and processes for their preparation.

EXAMPLE 1

2-(Chloromethyl)pyridine hydrochloride (16.3 g., 0.1 mole) is dissolved in 100 ml. of methanol. Freshly prepared sodium methoxide (5 g., 0.22 mole of sodium dissolved in 150 ml. of methanol) is added dropwise. The resulting mixture is heated at reflux for 18 hours, then filtered. The filtrate is concentrated. Water and ether are added, the aqueous phase is extracted with ether and the combined ethereal phases are washed with water and saturated aqueous sodium chloride, then dried over magnesium sulfate, concentrated and distilled to give 2-(methoxymethyl)pyridine.

Alternatively, 0.1 mole of 2-(chloromethyl)pyridine and 0.11 mole of sodium methoxide are used in the above procedure to give 2-(methoxymethyl)pyridine.

Also, 2-(methoxymethyl)pyridine is prepared by the following alternative procedure. A mixture of 10.9 g. of 2-pyridinemethanol and 2.4 g. of sodium hydride in 50 ml. of dimethylsulfoxide is warmed on a steam bath for 15 minutes, then cooled to room temperature. Methyl iodide (14.2 g.) is added and then the mixture is heated at 40°C. for 1 hour. Water (150 ml.) is then added and the mixture is extracted with ether. The extracts are dried, concentrated and distilled to give 2-(methoxymethyl)pyridine.

2-(Methoxymethyl)pyridine (4.4 g., 0.036 mole), dissolved in 25 ml. of dry benzene, is added dropwise to 20 ml. of 2M phenyl lithium (0.04 mole) in benzene/ether with cooling. The mixture is stirred for 30 minutes, then methyl isothiocyanate (2.6 g., 0.03 mole), dissolved in 40 ml. of dry benzene, is added dropwise with cooling. The resulting solution is stirred overnight. An equal volume of water is added and the solution is cooled and made acidic with 10% hydrochloric acid. The phases are separated, the organic phase is washed with water and the combined aqueous phases are made basic to about pH 9, then extracted with chloroform. The chloroform extracts are washed with water and dried over magnesium sulfate. Filtration and removal of solvent gives a residue which is recrystallized from isopropyl ether/ethanol to give 2-methoxy-N-methyl-2-(2-pyridyl)thicacetamide, m.p. 104°–105°C.

EXAMPLE 2

By the procedure of Example 1, using in place of sodium methoxide, the following sodium alkoxides:
  sodium ethoxide
  sodium propoxide
  sodium butoxide
  sodium allyloxide
  sodium cyclopropanemethoxide
the products are, respectively:
  2-ethoxy-N-methyl-2-(2-pyridyl)thioacetamide
  N-methyl-2-propoxy-2-(2-pyridyl)thioacetamide
  2-butoxy-N-methyl-2-(2-pyridyl)thioacetamide
  2-allyloxy-N-methyl-2-(2-pyridyl)thioacetamide
  2-cyclopropanemethoxy-N-methyl-2-(2-pyridyl)thioacetamide.

EXAMPLE 3

By the procedure of Example 1, using in place of 2-(chloromethyl)pyridine, the following:
  2-(chloromethyl)pyrazine
  2-(chloromethyl)quinoline
  2-(chloromethyl)thiazole
  4-(chloromethyl)thiazole
the products are, respectively:
  2-methoxy-N-methyl-2-(2-pyrazinyl)thioacetamide
  2-methoxy-N-methyl-2-(2-quinolyl)thioacetamide
  2-methoxy-N-methyl-2-(2-thiazolyl)thioacetamide
  2-methoxy-N-methyl-2-(4-thiazolyl)thioacetamide.

EXAMPLE 4

A mixture of 6.3 g. of 2-pyrrolemethanol and 25 ml. of thionyl chloride is heated on a steam bath for 4 hours. The mixture is then concentrated under reduced pressure and the residue is dissolved in water, basified with 5% aqueous sodium bicarbonate solution and extracted with ether. The extracts are dried, concentrated and distilled to give 2-(chloromethyl)-pyrrole.

Using 2-(chloromethyl)pyrrole in place of 2-(chloromethyl)pyridine in the procedure of Example 1 gives 2-methoxy-N-methyl2-(2-pyrrolyl)thioacetamide.

In the same manner, converting 2-pyrimidinemethanol to 2-(chloromethyl)pyrimidine and using 2-(chloromethyl)-pyrimidine in the procedure of Example 1, the product is 2-methoxy-N-methyl-2-(2-pyrimidyl)thioacetamide.

EXAMPLE 5

4-Pyrimidinecarboxylic acid is reduced using lithium aluminum hydride in ether to give 4-pyrimidinemethanol.

4-Pyrimidinemethanol is converted to 4-(chloromethyl)-pyrimidine by the procedure of Example 4.

Using 4-(chloromethyl)pyrimidine in the procedure of Example 1, the product is 2-methoxy-N-methyl-2-(4-pyrimidyl)-thioacetamide.

EXAMPLE 6

To a solution containing 12.1 g. (0.08 mole) of methyl 2-(2-pyridyl)acetate in 120 ml. of carbon tetrachloride is added 14.8 g. (0.084 mole) of N-bromosuccinimide and 0.3 g. of dibenzoylperoxide. The solution is irradiated by means of a sun-lamp source until essentially all the solid (succinimide) has risen to the top (about 10–15 minutes).

The solution is filtered and the solvent is removed under reduced pressure and without heat to give methyl 2-bromo-2-(2-pyridyl)acetate.

The above prepared 2-bromo compound is dissolved in 100 ml. of dry methanol and freshly prepared sodium methoxide (0.09 mole) in 100 ml. of dry methanol is added dropwise. Then the mixture is stirred for 3 hours at room temperature. The solvent is removed under reduced pressure and without heat to give methyl 2-methoxy-2-(2-pyridyl)acetate.

The above prepared 2-methoxy compound is dissolved in 65 ml. of concentrated ammonium hydroxide and the solution is stirred for 6.5 hours. The mixture is then concentrated, dissolved in chloroform and extracted twice with brine. The organic phase is dried over magnesium sulfate and filtered and solvent is removed under reduced pressure to give 2-methoxy-2-(2-pyridyl)acetamide.

To 20 ml. of dry 1,2-dichloroethane containing 2.0 g. of sodium chloride is added 3.32 g. of 2-methoxy-2-(2-pyridyl)-acetamide. After stirring at room temperature for 15 minutes, 1.7 ml. of phosphorus oxychloride is added. The solution is refluxed for 18 hours. The solution is then cooled and made basic with 10% aqueous sodium hydroxide solution. The aqueous phase is extracted three times with chloroform and the combined chloroform extracts are washed three times with water and once with brine and dried over magnesium sulfate. Filtration, removal of solvent and distillation in vacuo gives 2-methoxy-2-(2-pyridyl)acetonitrile, b.p. 72°–76°C./0.2 mm.

In 125 ml. of dry pyridine containing 4 ml. of triethylamine is dissolved 2.65 g. (0.018 mole) of 2-methoxy-2-(2-pyridyl)acetonitrile. Hydrogen sulfide is bubbled through the solution for 5.5 hours. The solvent is evaporated under reduced pressure and chloroform is added to the residue. The mixture is allowed to stand at −20°C. for 18 hours. The precipitate is filtered off and recrystallized from isopropanol to give 2-methoxy-2-(2-pyridyl)thioacetamide, m.p. 157°–159°C.

EXAMPLE 7

By the procedure of Example 6, using in place of methyl 2-(2-pyridyl)acetate, the following:
  methyl 2-(2-pyrrolyl)acetate
  ethyl 2-(2-quinolyl)acetate
  ethyl 2-(4-thiazolyl)acetate
  ethyl 2-(4-methyl-2-thiazolyl)acetate
  ethyl 2-(3-methyl-2-pyrazinyl)acetate
the products are, respectively:
  2-methoxy-2-(2-pyrrolyl)thioacetamide
  2-methoxy-2-(2-quinolyl)thioacetamide
  2-methoxy-2-(4-thiazolyl)thioacetamide
  2-methoxy-2-(4-methyl-2-thiazolyl)thioacetamide
  2-methoxy-2-(3-methyl-2-pyrazinyl)thioacetamide.

EXAMPLE 8

2-(4-Pyrimidyl)acetic acid is converted to the corresponding methyl ester by mixing with methanol, cooling and bubbling in hydrogen chloride, then basifying the mixture, extracting with chloroform and removing the solvent from the extracts. Using the resulting methyl 2-(4-pyrimidyl)acetate in the procedure of Example 6 gives 2-methoxy-2-(4-pyrimidyl)thioacetamide.

EXAMPLE 9

A mixture of 7.2 g. of 2-pyrimidinemethanol and 25 ml. of thionyl chloride is heated for 4 hours on a steam bath, then concentrated under reduced pressure. The residue is dissolved in water and basified with 5% aqueous sodium bicarbonate solution. Extracting with ether, then drying and concentrating the extracts gives 2-(chloromethyl)pyrimidine.

A solution of 6.8 g. of 2-(chloromethyl)pyrimidine is added dropwise to a solution of 5.2 g. of sodium cyanide in 100 ml. of dimethylsulfoxide. The mixture is heated at 50°C. for 2 hours, then diluted with 150 ml. of 5% aqueous sodium carbonate solution and extracted with ether. The extract is dried and concentrated to give 2-(2-pyrimidyl)acetonitrile.

A mixture of 2-(2-pyrimidyl)acetonitrile, concentrated sulfuric acid (two molar equivalents) and methanol is heated at reflux for 6 hours, then concentrated and basified with aqueous sodium carbonate solution. Extracting with chloroform, then concentrating and distilling the extracts under reduced pressure gives methyl 2-(2-pyrimidyl)acetate.

Using methyl 2-(2-pyrimidyl)acetate in the procedure of Example 6, the product is 2-methoxy-2-(2-pyrimidyl)thioacetamide.

In the same manner, from 2-(chloromethyl)pyrazine, the product is 2-methoxy-2-(2-pyrazinyl)thioacetamide.

Similarly, from 2-(chloromethyl)thiazole, the product is 2-methoxy-2-(2-thiazolyl)thioacetamide.

EXAMPLE 10

A solution of 9.1 g. of 2-methoxy-2-(2-pyridyl)-thioacetamide in a 40% aqueous solution of cyclopropylamine is heated at reflux for 45 minutes. The mixture is cooled and 30 ml. of water is added. The mixture is extracted with chloroform and the extracts are dried over magnesium sulfate and concentrated to give after recrystallizing the residue, N-cyclopropyl-2-methoxy-2-(2-pyridyl)thioacetamide.

By the same procedure, using the following cycloalkylamines:
  cyclobutylamine
  cyclopentylamine
  cyclohexylamine
the products are, respectively:
  N-cyclobutyl-2-methoxy-2-(2-pyridyl)thioacetamide
  N-cyclopentyl-2-methoxy-2-(2-pyridyl)thioacetamide
  N-cyclohexyl-2-methoxy-2-(2-pyridyl)thioacetamide.

EXAMPLE 11

Using cyclopropanemethyl isothiocyanate in place of methyl isothiocyanate in the procedure of Example 1 gives N-cyclopropanemethyl-2-methoxy-2-(2-pyridyl)-thioacetamide.

EXAMPLE 12

Alternatively, N-cyclopropanemethyl-2-methoxy-2-(2-pyridyl)thioacetamide is prepared by the following procedure.

A solution of 6.0 g. of cyclopropanemethylamine hydrochloride and 4.7 g. of sodium bicarbonate in 75 ml. of water is added to 5.4 g. of 2-methoxy-2-(2-pyridyl)thioacetamide. The reaction mixture is heated on a steam bath with stirring for 4 hours. The mixture is then cooled and 25 ml. of water is added. The reaction mixture is extracted three times with chloroform. The chloroform extracts are combined, dried over magnesium sulfate and then evaporated. The residue is purified by "dry-column" chromatography on silica gel, using ethyl acetate as solvent. The product is recrystallized to give N-cyclopropanemethyl-2-methoxy-2-(2-pyridyl)thioacetamide.

Similarly, using in place of cyclopropanemethylamine hydrochloride, the following:
  cyclobutanemethylamine hydrochloride
  cyclopentanemethylamine hydrochloride
  cyclohexanemethylamine hydrochloride
the products are, respectively:
  N-cyclobutanemethyl-2-methoxy-2-(2-pyridyl)thioacetamide
  N-cyclopentanemethyl-2-methoxy-2-(2-pyridyl)thioacetamide
  N-cyclohexanemethyl-2-methoxy-2-(2-pyridyl)thioacetamide.

EXAMPLE 13

By the procedure of Example 10, using in place of 2-methoxy-2-(2-pyridyl)thioacetamide, the following:
  2-methoxy-2-(2-pyrrolyl)thioacetamide
  2-methoxy-2-(2-quinolyl)thioacetamide
  2-methoxy-2-(2-pyrimidyl)thioacetamide
  2-methoxy-2-(4-thiazolyl)thioacetamide
the products are, respectively:

N-cyclopropyl2-methoxy-2-(2-pyrrolyl)thioacetamide

N-cyclopropyl-2-methoxy-2-(2-quinolyl)thioacetamide

N-cyclopropyl-2-methoxy-2-(2-pyrimidyl)thioacetamide

N-cyclopropyl-2-methoxy-2-(4-thiazolyl)thioacetamide.

Similarly, the corresponding N-cyclobutyl, N-cyclopentyl and N-cyclohexyl compounds are prepared.

EXAMPLE 14

By the procedure of Example 12, using the appropriate 2-alkoxy-2-heterocyclic-thioacetamide, the following products are prepared:

N-cyclopropanemethyl-2-methoxy-2-(2-pyrrolyl)thioacetamide

N-cyclopropanemethyl-2-methoxy-2-(2-quinolyl)thioacetamide

N-cyclopropanemethyl-2-methoxy-2-(2-pyrimidyl)-thioacetamide

N-cyclopropanemethyl-2-methoxy-2-(4-thiazolyl)-thioacetamide.

EXAMPLE 15

2-(Methoxymethyl)pyridine (1.85 g., 0.015 mole) in 15 ml. of dry benzene is added dropwise to a chilled solution of phenyl lithium (8.1 ml. of 2.1 molar solution, 0.017 mole) in 15 ml. of dry benzene. After the addition is complete, the mixture is stirred at 0°C. for 1 hour. Phenyl isothiocyanate (2.03 g., 0.015 mole) in 15 ml. of dry benzene is added dropwise and the mixture is allowed to come to room temperature gradually, then the mixture is stirred overnight. The mixture is diluted with 50 ml. of water and acidified with dilute hydrochloric acid. The layers are separated and the organic layer is washed several times with water. The aqueous layers are combined, basified with dilute aqueous sodium hydroxide solution and extracted several times with chloroform. The chloroform extracts are combined, washed once with brine and dried over magnesium sulfate. The solvent is removed under reduced pressure to give an oil which is placed on a silica gel "dry-column", eluting with ethyl acetate to give, after cooling and recrystallizing from ethyl acetate/hexane, 2-methoxy-N-phenyl-2-(2-pyridyl)-thioacetamide, m.p. 97°–98.5°C.

EXAMPLE 16

By the procedure of Example 6, using the appropriate sodium alkoxide in place of sodium methoxide, the following products are obtained:

2-ethoxy-2-(2-pyridyl)thioacetamide
2-propoxy-2-(2-pyridyl)thioacetamide
2-butoxy-2-pyridyl)thioacetamide
2-allyloxy-2-(2-pyridyl)thioacetamide
2-cyclopropanemethoxy-2-(2-pyridyl)thioacetamide.

EXAMPLE 17

2-Methoxy-N-methyl-2-(2-pyridyl)thioacetamide (500 mg.) in ether is added to ethereal hydrogen chloride. The resulting precipitate is filtered off and recrystallized from ethanol/ether to give 2-methoxy-N-methyl-2-(2-pyridyl)thioacetamide hydrochloride.

By the same procedure, the hydrochloride salt of 2-methoxy-2-(2-pyridyl)thioacetamide is prepared.

EXAMPLE 18

One gram of 2-methoxy-2-(2-pyridyl)thioacetamide in ethanol to give, after removing the solvent under reduced pressure, 2-methoxy-2-(2-pyridyl)thioacetamide maleate.

In the same manner, using citric acid, the citrate salt of 2-methoxy-2-(2-pyridyl)thioacetamide is prepared.

EXAMPLE 19

To a stirred solution of 11.8 g. (0.1 mole) of 2-pyridylacetonitrile in dry dimethylsulfoxide at 10°C. is added 0.1 mole of sodium hydride (dispersed in mineral oil). After 20 minutes, 0.1 mole of chloromethyl methyl ether is added with cooling and the mixture is kept at 10°C. for 2 hours, then allowed to warm to room temperature overnight. The reaction mixture is poured into water and extracted with ether. The organic phase is washed with water, dried over anhydrous sodium sulfate, concentrated under vacuum and distilled to give 3-methoxy-2-(2-pyridyl)propionitrile.

2 grams of 3-methoxy-2-(2-pyridyl)propionitrile is dissolved in 1.5 g. of triethylamine and 2 g. of dry pyridine, saturated with hydrogen sulfide. The mixture is heated at 100°C. in a sealed bomb for 15 hours. The mixture is cooled, diluted with water and extracted with ether. The organic phase is dried, the solvent is removed and the residue is recrystallized from benzene/petroleum ether to give 3-methoxy-2-(2-pyridyl)-thiopropanamide.

EXAMPLE 20

By the procedure of Example 19, using in place of 2-pyridylacetonitrile, the following:
2-pyrimidylacetonitrile
4-thiazolylacetonitrile
the products are, respectively:
3-methoxy-2-(2-pyrimidyl)thiopropanamide
3-methoxy-2-(4-thiazolyl)thiopropanamide.

EXAMPLE 21

By the procedure of Example 19, using 2-bromoethyl ethyl ether in place of chloromethyl methyl ether, the product is 4-ethoxy-2-(2-pyridyl)thiobutanamide.

Similarly, using 2-bromoethyl methyl ether, the product is 4-methoxy-2(2-pyridyl)thiobutanamide.

EXAMPLE 22

In the procedure of Example 1, using the following in place of methyl isothiocyanate:
ethyl isothiocyanate
propyl isothiocyanate
butyl isothiocyanate
the products are, respectively:
N-ethyl-2-methoxy-2-(2-pyridyl)thioacetamide
2-methoxy-N-propyl-2-(2-pyridyl)thioacetamide
N-butyl-2-methoxy-2-(2-pyridyl)thioacetamide.

EXAMPLE 23

A mixture of 18.1 g. of methyl 2-methoxy-2-(2-pyrridyl)acetate and 10 g. of dimethylamine in ethanol is stirred at room temperature for 26 hours. The mixture is concentrated, dissolved in chloroform and extracted with brine. The organic phase is dried over magnesium sulfate and filtered and the solvent is removed under reduced pressure to give 2-methoxy-N,N-dimethyl2-(2-pyridyl)acetamide.

Alternatively, 2-methoxy-N,N-dimethyl-2-pyridyl)acetamide is prepared by the following procedure.

2-Methoxy-2-(2-pyridyl)acetyl chloride hydrochloride, 22 g., [prepared by reacting 2-methoxy-2-(2-pyridyl)acetic acid in benzene with thionyl chloride] in 100 ml. of chloroform is added dropwise and with cooling to 50 g. of dimethylamine in 100 ml. of chloroform. The mixture is stirred for 4 hours, then 50 ml. of 5% aqueous sodium hydroxide is added and the chloroform solution is dried and concentrated to give 2-methoxy-N,N-dimethyl-2-(2-pyridyl)acetamide.

Phosphorus pentasulfide (4 g.) is added to 9.7 g. of 2-methoxy-N,N-dimethyl-2-(2-pyridyl)acetamide in 25 ml. of pyridine. The mixture is heated on a steam bath for 2 hours, then 250 ml. of water and 10 ml. of 5% aqueous sodium hydroxide solution are added. The mixture is extracted with chloroform and the extracts are dried and concentrated and the residue is recrystallized to give 2-methoxy-N,N-dimethyl-2-(2-pyridyl)thioacetamide.

EXAMPLE 24

Alternatively, 2-methoxy-N,N-dimethyl-2-(2-pyridyl)thioacetamide is prepared by the following procedures.

To 0.10 mole of phenyl lithium in 100 ml. of benzene/ether at 0°C. is added dropwise 10.6 g. (0.084 mole) of 2-(methoxymethyl)pyridine dissolved in 75 ml. of benzene. To this mixture is added dropwise 10.0 g. (0.081 mole) of N,N-dimethylthiocarbamoyl chloride in 100 ml. of benzene. The resulting mixture is stirred at room temperature overnight, then poured into 100 ml. of water and acidified. The organic phase is extracted once with dilute aqueous acid. The combined aqueous phases are extracted twice with ether, then made basic to about pH 10 and extracted three times with chloroform. The combined chloroform extracts are dried over magnesium sulfate and the solvent is removed by evaporation. The residue is chromatographed, then distilled in vacuo to give 2-methoxy-N,N-dimethyl-2-(2-pyridyl)thioacetamide.

Alternatively, using N,N-dimethylcarbamoyl chloride in the above procedure gives 2-methoxy-N,N-dimethyl-2-(2-pyridyl)acetamide which is converted to the thioacetamide by reaction with phosphorus pentasulfide by the procedure described in Example 23.

EXAMPLE 25

Using the following N,N-di-lower alkylthiocarbamoyl chloride compounds in the procedure of Example 24:
N,N-diethylthiocarbamoyl chloride
N,N-dipropylthiocarbamoyl chloride
N,N-dibutylthiocarbamoyl chloride
the products are, respectively:
N,N-diethyl-2-methoxy-2-(2-pyridyl)thioacetamide
2-methaoxy-N,N-dipropyl-2-(2-pyridyl)thioacetamide
N,N-dibutyl-2-methoxy-2-(2-pyridyl)thioacetamide.

EXAMPLE 26

To a solution of 110 g. of sodium borohydride in 1250 ml. of methanol at 0°C. is added 350 g. of 2-pyridyl methyl ketone in 300 ml. of methanol with stirring. After stirring for 4 hours at 0°–5°C., glacial acetic acid is cautiously added dropwise, followed by ice and concentrated hydrochloric acid. The acidic solution is made basic with aqueous sodium hydroxide and extracted with dichloromethane. The organic layer is dried over magnesium sulfate, concentrated and distilled to give 1-(2-pyridyl)ethanol.

To a stirred solution of 223 g. of 1-(2-pyridyl)ethanol in 1500 ml. of dry dimethylsulfoxide is added 2.3 moles of sodium hydride in portions, under nitrogen, maintaining the temperature at 20°C. After two hours, 331 g. of methyl iodide is added at 20°C. After stirring for another 3 hours, the mixture is poured onto ice-water and extracted three times with ether. The organic phase is washed with water, dried over magnesium sulfate, concentrated in vacuo, and the residue is distilled to give 2-(1-methoxyethyl)pyridine.

To a solution containing 0.42 moles of phenyl lithium in 400 ml. of dry ether under nitrogen, is added 57.5 g. of 2-(1-methoxyethyl)pyridine in 50 ml. of dry ether at −10°C. over 20 minutes. After stirring another 15 minutes at −10°C, a solution of 52 g. of N,N-dimethylthiocarbamoyl chloride in 150 ml. of benzene-ether (3:2) is added. The mixture is stirred for 3 hours at −10°C. and poured into ice-water.

Ice cold 6N hydrochloric acid is added until the mixture is acidic, and the aqueous phase is separated, washed twice with cold dichloromethane and made basic with aqueous sodium hydroxide solution. The mixture is extracted with dichloromethane and the organic phase is dried over magnesium sulfate and the solvent is removed in vacuo. The residue is decolorized with charcoal in benzene and recrystallized to give 2-methoxy-N,N-dimethyl-2-(2-pyridyl)thiopropanamide, m.p. 67.8°–70°C.

2-Pyridyl ethyl ketone (prepared by adding 2-pyridinecarbonitrile in tetrahydrofuran to ethyl magnesium chloride in ether, refluxing for 24 hours, pouring onto ice, adding 25% sulfuric acid, then basifying, extracting with ether and drying and concentrating the extracts) is used in place of 2-pyridyl methyl ketone in the above procedure to give 2-methoxy-N,N-dimethyl-2-(2-pyridyl)thiobutanamide.

Similarly, using 2-pyridyl butyl ketone (prepared from 2-pyridinecarbonitrile and butyl magnesium chloride by the above procedure) in place of 2-pyridyl methyl ketone, the product is 2-methoxy-N,N-dimethyl-2-(2-pyridyl)thiohexanamide.

In the same manner, using in the above procedure, the following heterocyclic alkyl ketones:
2-quinolyl methyl ketone
4-pyrimidyl methyl ketone
2-thiazolyl methyl ketone
the products are, respectively:
2-methoxy-N,N-dimethyl-2-(2-quinolyl)thiopropanamide
2-methoxy-N,N-dimethyl-2-(4-pyrimidyl)thiopropanamide
2-methoxy-N,N-dimethyl-2-(2-thiazolyl)thiopropanamide.

EXAMPLE 27

| Ingredient | Amount |
| --- | --- |
| 2-Methoxy-N-methyl-2-(2-pyridyl)-thioacetamide hydrochloride | 100 mg. |
| Lactose | 100 mg. |
| Magnesium stearate | 5 mg. |

The ingredients are mixed and filled into a hard gelatin capsule.

EXAMPLE 28

| Ingredient | Amount |
| --- | --- |
| 2-Methoxy-N,N-dimethyl-2-(2-pyridyl)-thioacetamide | 150 mg. |
| Calcium sulfate dihydrate | 125 mg. |
| Sucrose | 25 mg. |
| Starch | 15 mg. |
| Talc | 5 mg. |
| Stearic acid | 3 mg. |

The sucrose, calcium sulfate dihydrate and 2-methoxy-N,N-dimethyl-2-(2-pyridyl)thioacetamide are thoroughly mixed and granulated with 10% gelatin solution. The wet granules are screened, dried and then mixed with the starch, talc and stearic acid, screened and compressed into a tablet.

The compositions prepared as in Examples 27 and 28 are administered orally to a subject having excessive gastric acid secretion within the dose ranges given hereabove.

What we claim is:

1. A pharmaceutical composition having gastric acid secretion inhibitory activity, in dosage unit form, comprising a pharmaceutical carrier and an effective amount of a thioamide compound of the formula:

$$\begin{array}{c} R_4 \;\; S \\ | \;\;\;\; \| \\ R_1-C-C-R_3 \\ | \\ (CH_2)_m \\ | \\ O-R_2 \end{array}$$

in which:
 $m$ is 0, 1, or 2;
 $R_1$ is 2-pyridyl
 $R_2$ is lower alkyl, allyl or cyclopropanemethyl;
 $R_3$ is $$N\!\!\begin{array}{c}\diagup R_5 \\ \diagdown R_6 \end{array},$$

NH-phenyl or NH-$(CH_2)_n$-cycloalkyl, said cycloalkyl having 3-6 carbon atoms;
 $R_4$ is hydrogen or lower alkyl;
 $R_5$ and $R_6$ are hydrogen or lower alkyl and
 $n$ is 0 or 1
or a pharmaceutically acceptable acid salt thereof.

2. A pharmaceutical composition of claim 1 in which $R_4$ is hydrogen.

3. A pharmaceutical composition of claim 1 in which $m$ is 0.

4. A pharmaceutical composition of claim 1 in which the thioamide compound is 2-methoxy-N-methyl-2-(2-pyridyl)thioacetamide.

5. A pharmaceutical composition of claim 1 in which the thioamide compound is 2-methoxy-N,N-dimethyl-2-(2-pyridyl)thiopropanamide.

6. A pharmaceutical composition of claim 1 in which the thioamide compound is present in an amount of from about 10 mg. to about 500 mg.

7. A method of inhibiting gastric acid secretion in an animal in need of said treatment which comprises administering to said animal an effective gastric acid secretion inhibiting amount of a thioamide compound of the formula:

$$\begin{array}{c} R_4 \;\; S \\ | \;\;\;\; \| \\ R_1-C-C-R_3 \\ | \\ (CH_2)_m \\ | \\ O-R_2 \end{array}$$

in which:
 $m$ is 0, 1 or 2;
 $R_1$ is 2-pyridyl;
 $R_2$ is lower alkyl, allyl or cyclopropanemethyl;
 $R_3$ is $$N\!\!\begin{array}{c}\diagup R_5 \\ \diagdown R_6 \end{array},$$

NH-phenyl or NH-$(CH_2)_n$-cycloalkyl, said cycloalkyl having 3–6 carbon atoms;
 $R_4$ is hydrogen or lower alkyl;
 $R_5$ and $R_6$ are hydrogen or lower alkyl and
 $n$ is 0 or 1
or a pharmaceutically acceptable acid addition salt thereof.

8. A method of claim 1 in which $R_4$ is hydrogen.

9. A method of claim 1 in which $m$ is 0.

10. A method of claim 1 in which the thioamide compound is 2-methoxy-N-methyl-2-(2-pyridyl)thioacetamide.

11. A method of claim 1 in which the thioamide compound is 2-methoxy-N,N-dimethyl-2-(2-pyridyl)-thiopropanamide.

12. A method of claim 1 in which the thioamide compound is administered in a daily dosage of from about 10 mg. to about 2500 mg.

* * * * *

UNITED STATES PATENT AND TRADEMARK OFFICE
CERTIFICATE OF CORRECTION

PATENT NO. : 3,966,945
DATED : June 29, 1976
INVENTOR(S) : Helene E. Bowman Van Hoeven, L. Martin Brenner and Bernard Loev It is certified that error appears in the above-identified patent and that said Letters Patent are hereby corrected as shown below:

Column 2, line 28, "an" should read -- on -- .

Column 2, lines 33-35, that portion of the right-hand structure reading

Column 10, line 4, after "ethanol" insert -- is treated with an equimolar amount of maleic acid in ethanol -- .

Column 11, line 54, "2-methaoxy" should read -- 2-methoxy --.

Signed and Sealed this

Twenty-first Day of September 1976

[SEAL]

Attest:

RUTH C. MASON
Attesting Officer

C. MARSHALL DANN
Commissioner of Patents and Trademarks